(12) United States Patent
Petters et al.

(10) Patent No.: US 9,850,185 B2
(45) Date of Patent: Dec. 26, 2017

(54) METHOD AND SYSTEM FOR ACETYLENE ($C_2H_2$) OR ETHYLENE ($C_2H_4$) PRODUCTION

(71) Applicant: Bestrong International Limited, Hong Kong (HK)

(72) Inventors: Stefan Petters, Vienna (AT); Klaus Mauthner, Vienna (AT); Ka Chun Tse, Hong Kong (HK)

(73) Assignee: Bestrong International Limited, Hong Kong (HK)

( * ) Notice: Subject to any disclaimer, the term of this patent is extended or adjusted under 35 U.S.C. 154(b) by 0 days.

(21) Appl. No.: 14/949,130

(22) Filed: Nov. 23, 2015

(65) Prior Publication Data

US 2016/0152528 A1    Jun. 2, 2016

(30) Foreign Application Priority Data

Dec. 1, 2014   (EP) .................................... 14195574

(51) Int. Cl.
*C07C 1/00* (2006.01)
*C10H 15/00* (2006.01)
(Continued)

(52) U.S. Cl.
CPC .................. *C07C 5/09* (2013.01); *C01B 3/12* (2013.01); *C01B 3/24* (2013.01); *C10H 19/00* (2013.01);
(Continued)

(58) Field of Classification Search
CPC .. C07C 1/00; C10H 15/00; C10B 3/24; C10B 31/02; C10B 31/18; C10B 31/20; C10B 31/32; C10B 3/26
(Continued)

(56) References Cited

U.S. PATENT DOCUMENTS 2,845,329 A * 7/1958 Neubauer ............... C01B 31/32
423/421
3,468,794 A * 9/1969 Clifford .................. C02F 3/286
210/608
(Continued)

FOREIGN PATENT DOCUMENTS

WO        0226378 A1    4/2002

OTHER PUBLICATIONS

"Sabatier Reaction"; Wikipedia Search 1; Apr. 2013.*
(Continued)

*Primary Examiner* — Thuan D Dang
(74) *Attorney, Agent, or Firm* — Heslin Rothenberg Farley & Mesiti, P.C.; Melvin S. Li; Kristian E. Ziegler (57) ABSTRACT

The present invention is concerned with a method of production of acetylene or ethylene. The method has the steps of providing supplies of hydrogen, water, carbon monoxide, carbon dioxide, and methane, respectively, providing a catalyst system having firstly a catalyst selected from group VIII transition metal oxides, and secondly a catalyst support, treating the methane supply with the catalyst system for producing a first reactant, providing a second reactant, and reacting the first reactant with the second reactant for producing an intermediate, wherein the intermediate is calcium carbide ($CaC_2$).

14 Claims, 4 Drawing Sheets

(51) Int. Cl.
    *C10B 31/02*     (2006.01)
    *C07C 5/09*     (2006.01)
    *C10H 19/00*     (2006.01)
    *C10H 21/10*     (2006.01)
    *C01B 3/12*     (2006.01)
    *C01B 3/24*     (2006.01)

(52) U.S. Cl.
    CPC ...... C10H 21/10 (2013.01); *C01B 2203/0266* (2013.01); *C01B 2203/0283* (2013.01); *C01B 2203/06* (2013.01); *C01B 2203/1241* (2013.01); *Y02P 20/129* (2015.11)

(58) Field of Classification Search
    USPC ..... 48/59, 198.1, 216, 197 A; 585/534, 638, 585/733; 423/445 R, 441, 442, 650, 653, 423/654, 655, 418.2, 437.2
    See application file for complete search history.

(56) References Cited

U.S. PATENT DOCUMENTS

| | | |
|---|---|---|
| 5,472,581 A | 12/1995 | Wan |
| 6,767,375 B1* | 7/2004 | Pearson ................... C10J 3/485 48/111 |
| 2006/0177659 A1* | 8/2006 | Chen ...................... B01D 53/02 428/403 |

OTHER PUBLICATIONS

"Water-Gas Shift Reaction"; Wikipedia Search 2; Nov. 2013.*
"Boudouard Reaction"; Wikipedia Search 3; Jul. 2012.*
Shaobin Wang et al., "Carbon Dioxide Reforming of Methane to Produce Synthesis Gas over Metal-Supported Catalysts: State of the Art", Energy & Fuels, 10, pp. 896-904 (1996).

\* cited by examiner

METHOD AND SYSTEM FOR ACETYLENE ($C_2H_2$) OR ETHYLENE ($C_2H_4$) PRODUCTION

CROSS REFERENCE TO RELATED APPLICATIONS

This application claims priority under 35 U.S.C. §119 to European Patent Application No. EP 14195574.0, filed Dec. 1, 2014, which is hereby incorporated herein by reference in its entirety.

FILED OF THE INVENTION

The present invention is concerned with a method and system for production of acetylene ($C_2H_2$) or ethylene ($C_2H_4$). More particularly, the present invention is concerned with a method and a system for converting organic wastes into acetylene and/or ethylene.

BACKGROUND OF THE INVENTION

Acetylene and ethylene are hydrocarbons with the formula $C_2H_2$ and $C_2H_4$, respectively. They are widely used in chemical industry, and their worldwide production exceeds that of any other organic compound. In the United States and Europe alone, approximately 90% of ethylene is used to produce ethylene oxide, ethylene dichloride, ethyl benzene and polyethylene. Methane, carbon monoxide and hydrogen can be used as raw material gases for producing ethylene. Major industrial reactions of ethylene include the preparation of polymers via polymerization and these polymers all generated from crude oil steam cracking at 750-950° C.

One common practice to handle organic waste residues from municipal or industrial today is by anaerobic digestion and gasification. The outputs of these processes include carbon monoxide (CO), hydrogen ($H_2$), methane ($CH_4$) and carbon dioxide ($CO_2$). Carbon monoxide (CO), hydrogen ($H_2$), methane ($CH_4$) are often used to generate electricity. The generated electricity will either be consumed on site or feed to the grid to public. However, the electricity generated in the past can only provide less than 1% of local consumption. Feeding electricity generated only to the grid is not competitive at arm's length prices. This leads to processing of organic wastes in this manner as being economically unattractive. Recovering electrical energy from carbon monoxide (CO), hydrogen ($H_2$) and methane ($CH_4$) are typically regarded as low base-load and more costly than hydro-, wind- and nuclear-electricity generation. As a consequence, lower income regions do not harvest these gases and they often are just released to the atmosphere. These carbon containing gases, i.e. $CH_4$, CO and $CO_2$, will contribute to the atmospheric carbon stock or content or in other words as greenhouse gases. However, this would increase carbon content in the atmosphere, and is considered as detrimental to the world climate. Therefore, our environment needs a new method to capture carbon from organic end of life-cycle matter and re-capture carbons which are already released to the atmosphere.

Since there is large demand in acetylene but big supply in the raw material gas for acetylene or ethylene production which could be supplied from decomposition of organic matter into energy rich gases by anaerobic digestion and gasification, therefore, there is a potential in converting abundant organic matter into acetylene or ethylene in a close-loop system so that downstream chemical synthesis could be extended to the realization of Atmospheric Carbon Re-use.

The present invention seeks to produce acetylene or ethylene more effectively and efficiently, to capture carbon from organic end of life-cycle, to re-capture carbon which has already been released to the atmosphere, or to provide a useful alternative to the public.

SUMMARY OF THE INVENTION

According to a first aspect of the present invention, there is provided a method of converting organic wastes into acetylene or ethylene, comprising steps of a) providing supplies of hydrogen, water, carbon monoxide, and/or carbon dioxide, b) providing supply of methane, c) providing a catalyst system having firstly a catalyst selected from group VIII transition metal oxides, and secondly a catalyst support, d) treating the methane supply with the catalyst system for producing a first reactant, e) providing a second reactant; and f) reacting the first reactant with the second reactant for producing an intermediate, wherein the intermediate is calcium carbide ($CaC_2$). By organic wastes, it refers to undesirable discharge that is fermentable or combustible generated from domestic or industrial dwellings as wastes. These wastes were not reused effectively in the past.

Preferably, both the catalyst support and the second reactant may be calcium oxide.

In certain embodiments, the catalyst may be an oxide of nickel, cobalt, or iron, or a combination thereof.

In other embodiments, the catalyst may be selected from group VIII transition elements. The catalyst may be selected from a group including iron, nickel, cobalt, molybdenum and a mixture thereof.

Suitably, the catalyst support may be selected from a group including alkaline metal oxides, alkaline earth metal oxides, silicon, silicon oxides, aluminium oxides, silicon carbide, carbon and a mixture thereof. The catalyst support may have tubular or platelet morphology for increasing surface area thereof.

In an embodiment, the second reactant may be selected from a group including alkaline metal oxides, alkaline earth metal oxides, silicon, silicon oxides, aluminium oxides, silicon carbide, graphite and a mixture thereof.

Advantageously, the method may comprise a step of depositing said catalyst on the catalyst support by wet chemical impregnation of a solution with a group VIII transition metal oxide. In an embodiment, the catalyst may be deposited on catalyst support by decomposition of a volatile transition metal precursor complex comprising a step of depositing the catalyst on the catalyst support by decomposition of a volatile transition metal precursor. For example, metal in the metal precursor complex may have an oxidation state of zero.

In an embodiment, each of the methane supply and the carbon dioxide supply may be derived from both an external source and an internal source yielded during the acetylene or ethylene production, combination of the external and internal sources after reaction contributing said supplies of hydrogen, water, carbon monoxide, carbon dioxide, and methane, respectively, for consumption in the production method.

The method may comprise a step of acquiring a first energy containing feedstock substrate, wherein said first energy containing feedstock substrate includes fermentables. The fermentables may include sewage sludge, food and kitchen waste or a combination thereof. The method may comprise a step of subjecting the first energy containing feedstock substrate to anaerobic digestion for production of the carbon dioxide and the methane and for contribution to the external source of the carbon dioxide and the methane supplies, respectively.

The method may comprise step of acquiring a second energy containing feedstock substrate, wherein the second energy containing feedstock substrate includes combustibles. The combustibles may include refuse derived fuel, coal, biomass, fermentation digestible or a combination thereof.

Preferably, the second energy containing feedstock may have an input caloric value of at least 10 GJ/t.

The method may comprise a step of subjecting the second energy containing feedstock substrate to thermo-chemical treatment for production of the methane, the hydrogen, the carbon monoxide, and the carbon dioxide and for contribution to the external source of the methane, the hydrogen, the carbon monoxide, and the carbon dioxide, respectively.

The method may comprise, during formation of nano carbon in the above step d), cracking the methane supply for yielding a first internal source of the hydrogen, the first internal hydrogen source contributing to the hydrogen supply in the above step a).

The method may comprise, during formation of the calcium carbide ($CaC_2$), reacting the nano carbon with the calcium oxide for yielding the internal source of the carbon monoxide, the internal source of carbon monoxide contributing to the carbon monoxide supply.

The method may comprise a step of subjecting the carbon monoxide supply to water-gas shift reaction for yielding a second internal source of the hydrogen and a first internal source of the carbon dioxide, and the second internal source of hydrogen and the first internal source of carbon dioxide contributing to the hydrogen supply and the carbon dioxide supplies, respectively.

The method may comprise a step of subjecting the hydrogen supply and the carbon dioxide supply to Sabatier reaction, for yielding a first internal source of methane and the internal source of water, the first internal source of methane contributing to the methane supply and the internal source of water for contributing to the methane supply and the water supply, respectively.

The method may comprise a step of subjecting nano-carbon and the carbon dioxide supply to Boudouard reaction, for yielding carbon monoxide contributing to the carbon monoxide supply.

The method may comprise steps of splitting hydrocarbon gas and providing heating required in the splitting of hydrocarbon gas, wherein the heating is derived from waste heat internally or externally.

The method may comprise a step of reusing external hydrocarbon gas for production of methane contributing to the methane supply.

According to a second aspect of the present invention, there is provided a system for converting organic wastes into acetylene or ethylene, comprising a) reservoirs for supplies of hydrogen, water, carbon monoxide and/or carbon dioxide, b) reservoir for supply of methane, c) a catalyst system including a catalyst and a catalyst support for the catalyst, d) catalyst selected from group VIII transition metal oxides, e) a first reactor for treating the methane supply for producing a first reactant, f) a second reactor for reacting the second reactant with the first reactant for producing an intermediate, and wherein the catalyst support and the second reactant are both calcium oxide, and the intermediate is calcium carbide ($CaC_2$).

Preferably, each of the methane supply and the carbon dioxide supply may be derived from both an external source and an internal source yielded from operation of the production method, combination of the external and internal sources forming hydrogen, water, carbon monoxide, carbon dioxide, and methane, respectively, for consumption in said system.

BRIEF DESCRIPTION OF THE DRAWINGS

Some embodiments of the present invention will now be explained, with reference to the accompanied drawings, in which:—

DETAILED DESCRIPTION OF PREFERRED EMBODIMENTS OF THE INVENTION

One aspect of the present invention is concerned with a system for production of acetylene and ethylene. The system makes use of fermentable waste and/or combustible waste. The fermentable waste includes waste with high chemical oxygen demand value, for example sewage sludge and food & kitchen waste. Combustible waste is composited of biochemical stabilization sludge residues, non-recyclable organic municipal solid organic residues, mixed wastes, polymers, non-compostable (>10 mm) abundant end of life cycle biomass, and/or poor morphology coal fractions. The fermentable waste or combustible waste with respect to the present invention has average caloric value of at least 10 GJ/t.

When using the fermentable waste, the system allows anaerobic digestion of the waste for generation of gases including methane and carbon dioxide. When using combustible waste, the system allows gasification of the combustible waste for generation of gases including methane, carbon dioxide, hydrogen and carbon monoxide. The gases derived from the fermentable waste and the combustible waste together contribute to the gas supplies of carbon dioxide, carbon monoxide, hydrogen and methane. Since these gases are formed directly from the wastes input to the system, these gases generated from the wastes are considered as gases from an external source. These gaseous supplies are used as valuable intermediates for production of ethylene with higher added value, rather than seeking to use these gases or ethylene as alternatives to for example natural gas.

Reactions

The methane supply provides a source of methane, splitting of which in the presence of a catalyst system produces hydrogen and nano-carbon. The system is configured to allow these hydrogen and nano-carbon to contribute to the hydrogen supply, and the carbon dioxide and the carbon monoxide supplies, respectively. The catalyst system includes a catalyst and a catalyst support for the catalyst. In preferred embodiments, the catalyst is selected from a group including transition metals of nickel, cobalt and iron, and the catalyst support is selected from alkaline earth metal oxides, e.g. calcium oxide. Studies leading the present invention indicate that selection of these catalysts can yield carbon structure with different morphology in nanoscale. Example of these structures include but not limited to nanotube, carbon black, nano-onions, nanohoms and nanofibers. The following reaction (1) illustrates the catalytic splitting of hydrocarbon gas into hydrogen with the use of nickel as catalyst and calcium oxide (CaO) as catalyst support. Preparation of a catalyst system will be described later on in the description.

$$3\ CH_4 \xrightarrow{CaO/catalyst} 3\ \text{nano Carbon} + 6H_2 \tag{1}$$

In this reaction, nano carbon such as carbon nanotubes, is produced.

The system is configured to allow the produced nano carbon to further react with calcium oxide (CaO) for producing calcium carbide ($CaC_2$) and carbon monoxide (CO). This reaction is illustrated in the below reaction (2).

$$3\ \text{nano Carbon} + CaO \xrightarrow{2,300K} CO + CaC_2 \tag{2}$$

It is to be noted that the calcium oxide used in this reaction acts as reactant is also a catalyst support for the catalyst for converting methane from the methane supply to nano carbon and hydrogen.

The calcium carbide acts as an intermediate in the system and reacts with water from a water supply for producing acetylene ($C_2H_2$) which is an intermediate in the system and a predecessor of ethylene. Calcium hydroxide $Ca(OH_2)$ is also produced in below reaction (3).

$$CaC_2 + 2H_2O \rightarrow C_2H_2 + Ca(OH)_2 \tag{3}$$

The produced calcium hydroxide is an intermediate which is channeled back to a calcium hydroxide supply of the system. Since the calcium hydroxide is produced as a side product from within the system, it is considered as calcium hydroxide from an internal source. Calcium hydroxide from the calcium hydroxide supply is converted to calcium oxide in the present of heat, as shown in the following reaction (4).

$$Ca(OH)_2 \xrightarrow{heat} CaO \tag{4}$$

This calcium oxide contributes to the calcium oxide supply. It is to be noted that calcium oxide from the calcium supply acts as the catalyst support for the catalyst for production of nano carbon in reaction (1), and also as reactant in reaction (2) for production of calcium carbide and carbon dioxide. Since the calcium oxide in reaction (4) is produced as a side product in the system, it is considered as from an internal source.

The carbon monoxide supply received the carbon monoxide from both gasification of combustible and the carbon monoxide from reaction (2). In the system, the carbon monoxide supply provides carbon monoxide which undergoes water gas shift reaction (4) to generate more hydrogen and carbon dioxide as below reaction (5).

$$CO + H_2O \rightarrow CO_2 + H_2 \tag{5}$$

The carbon dioxide and the hydrogen produced in reaction (5) are channeled to the carbon dioxide supply and the hydrogen supply. Since the carbon dioxide and the hydrogen are produced as side products from within the system, they are considered as from an internal source. Carbon dioxide and hydrogen from the carbon dioxide supply and the hydrogen supply undergoes below Sabatier reaction (6) to generate as shown below.

$$CO_2 + 4H_2 \rightarrow 2H_2O + CH_4 \tag{6}$$

The methane and water are then channeled back to the water supply and the methane supply, respectively, in the system. Since the water and the methane in reaction (6) are produced as side products, they are considered as from internal source.

Acetylene produced in reaction (3) the above step can be subjected to hydrogenation reaction for production of ethylene as a final product gas. Please see below reaction (7).

$$C_2H_2 + H_2 \rightarrow C_2H_4 \tag{7}$$

Hydrogen from the hydrogen supply is derived from both hydrogen from gasification of the combustible and splitting of the methane in the presence of the catalytic system as described above in reaction (1). The hydrogen 223 produced from the gasification is considered hydrogen from an external source, while the hydrogen 216 produced as a side product in the system is considered hydrogen from an internal source.

Embodiments

Production of Ethylene in First Pathway in the System

Figure 1:
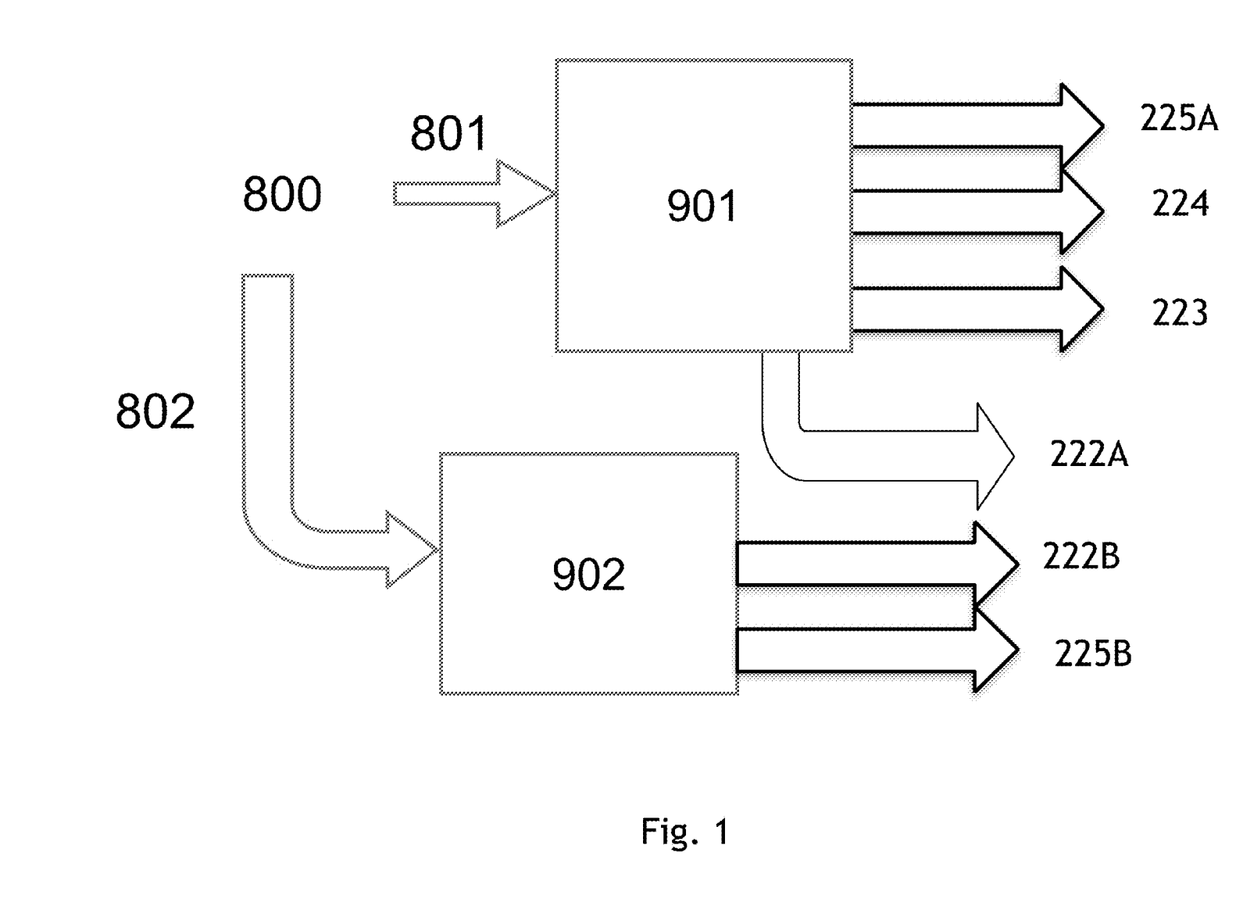
FIG. 1 is a schematic diagram devices for use in a system for converting combustibles and fermentables to raw material gases for production of ethylene, in according to the present invention.

FIG. 1 is a schematic diagram illustrating wastes 800 including combustibles 801 and fermentables 802. The combustibles may include refuse derived fuel (RDF) waste. The fermentables 802 may include sewage sludge, and food and kitchen (F&K) waste.

The combustibles 801 and fermentables 802 are treated separately. The combustibles 801 are fed into thermo-chemical treatment reactor 901 for generation of hydrogen 223, carbon monoxide 224, carbon dioxide 225A and methane 222A. The reactor 901 may be for example be a gasifier. The hydrogen 223, carbon monoxide 224, carbon dioxide 225A and methane 222A are channeled to supplies of hydrogen 109, carbon monoxide 114, carbon dioxide 115 and methane 110, respectively. Please also see FIG. 2. Please note that the terms "supply" and "reservoir" are herein used interchangeably.

The fermentables 802 are fed into anaerobic reactor 902 for generation of carbon dioxide 225B and methane 222B. The anaerobic reactor 902 may be an anaerobic digester. The carbon dioxide 225B and methane 222B are channeled to the supplies of carbon dioxide 115 and methane 110, respectively. Please also see FIG. 2.

Table 1 below illustrate quantities of outputs in an experiment using the system. Calculation is made based on a model of daily waste collected in a community.

TABLE 1

| | quantity (kg) | chemical energy | $CH_4$ (222A & 222B) output ($m^3$) | $H_2$ (223) output ($m^3$) | CO (224) output ($m^3$) | $CO_2$ (225A & 225B) output ($m^3$) |
|---|---|---|---|---|---|---|
| sewage sludge | 6,250 | 2.6 MW | 182 | | | 168 |
| F&K waste | 6,25 | 1.6 MW | 112 | | | 103 |
| RDF waste | 1,275 | 6.1 MW | 123 | 613 | 305 | 347 |
| total (solids) | 3,338 | | 417 | 613 | 305 | 618 |

Figure 2:
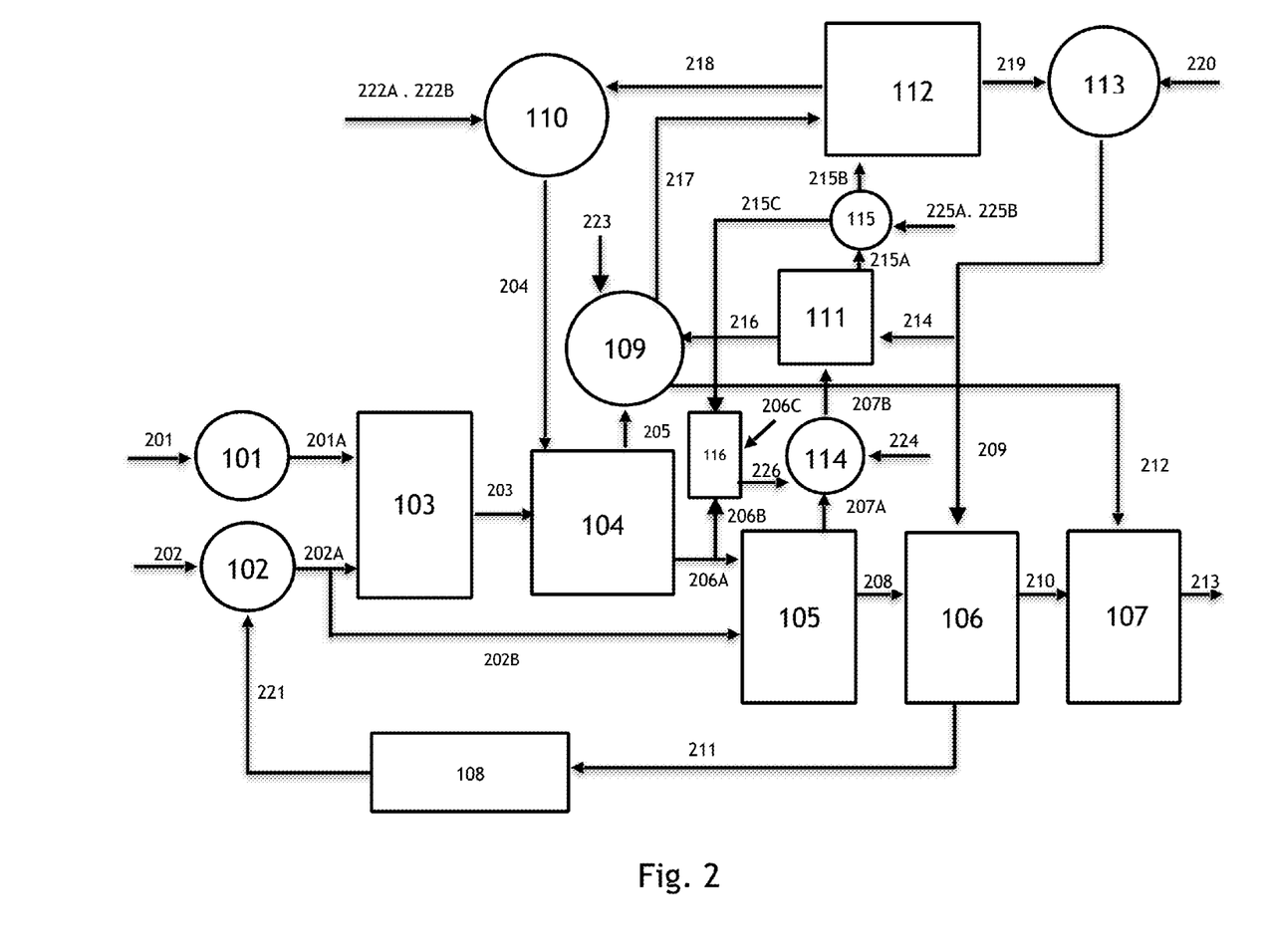
FIG. 2 is a schematic diagram illustrating the system for production of ethylene.
Figure 3:
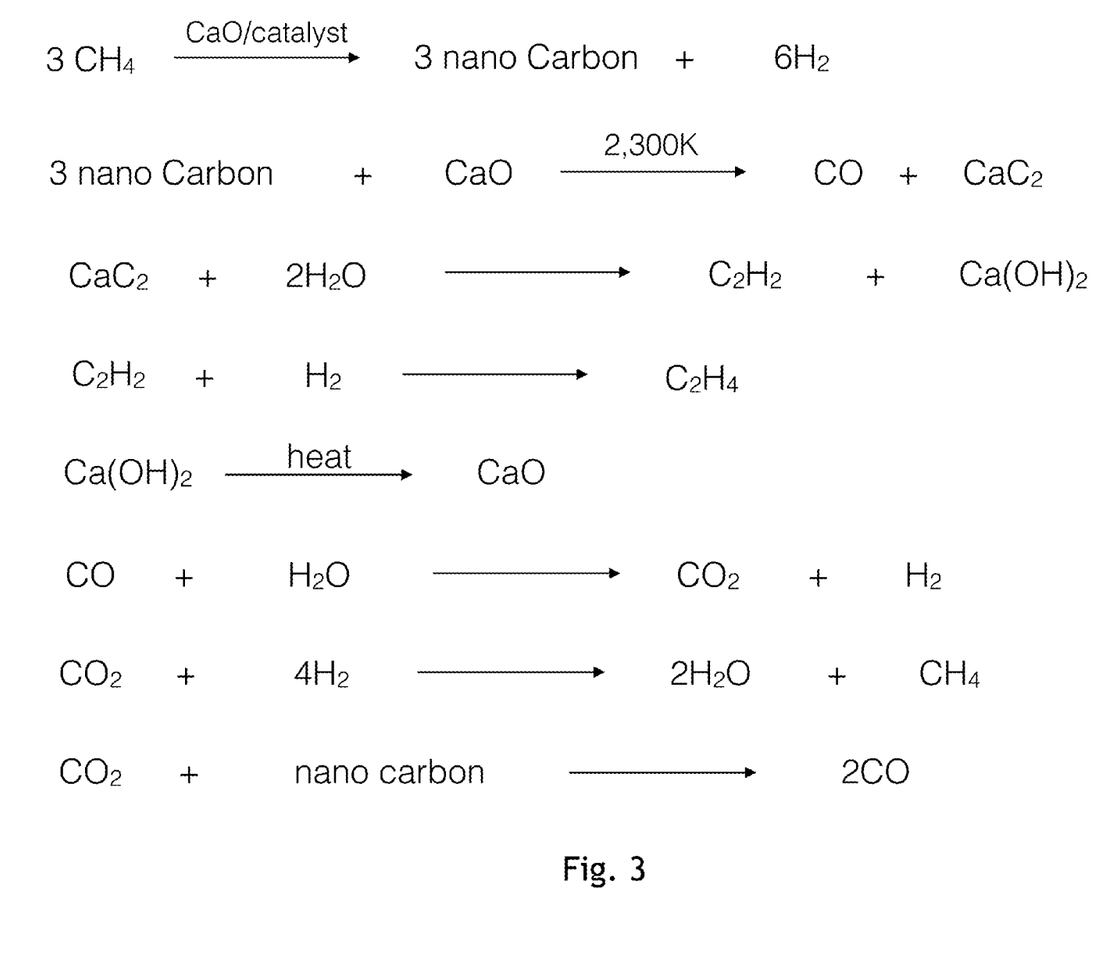
FIG. 3 is summary showing reactions occurring during operation of the system in FIG. 2.

FIG. 2 illustrates an embodiment of a system according to the present invention. The system comprises a chamber 101 fed with a catalyst 201 and for supplying catalyst 201A after optimization for usage in the system. The catalyst 201 is a transition metal catalyst. The system comprises a chamber 102 fed with a metal catalyst support 202 and for supplying optimized catalyst support 202A for usage in the system. The metal catalyst 201A and metal catalyst support 202A are fed into chamber 103 for mixing and optimization, forming catalyst 203 as an output. This catalyst 203 is used for catalytically splitting of methane gas 204 from the methane gas reservoir or supply 110. In a preferred embodiment, the system is configured to allow splitting of methane in chamber 104 at elevated temperature of 560° C.-850° C. The catalytic splitting of the methane in the chamber 104 yields hydrogen gas 205 and nano carbon 206A and 206B, hydrogen gas 205 is channeled to reservoir 109.

Reaction Occurred in the Reactor 104

TABLE 2

Quantities of feedstock and outputs in the reactor 104

| CH4 (204) | 417 m3 |
|---|---|
| nanocarbon (206A and 206B) | 208 kg |
| H2 (205) | 764 m3 |

Reaction Occurred in the Reactor 105

Nano carbon generated from the reactor 104 reacts with another reactant 202B for production of carbon monoxide 207A and calcium carbide 208. The reactant 202B is supplied from the chamber 102 and serves both as the reactant 202B and as the catalyst support 202A. The carbon monoxide 207A is channeled to the carbon monoxide supply or reservoir 114.

Reaction (8) below shows the reaction in reactor 105.

(8)

TABLE 3

Quantities of feedstock and outputs in the reactor 105

| nano carbon (206A) | 208 kg |
| CaO (202B) | 324 kg |

TABLE 3-continued

Quantities of feedstock and outputs in the reactor 105

| CaC2 (208) | 370 kg |
| CO (207A) | 162 m³ |

Thermal energy used for reaction in reactor 105 can be accomplished by the combustion of $H_2$, generated in the hydrocarbon splitting or from part of the feedstock inside reservoir 109. Eventually, the thermal energy required in reaction (8) can be internally supplied and could achieve high energy efficiency. The thermal energy input for the production of $CaC_2$ is ~3 kWh/kg, and as shown in Table 3, 370 kg of $CaC_2$ could be produced from 208 kg nano carbon and therefore, ~1,111 kWh is needed from $H_2$, equivalence to 375 $m^3$ of $H_2$.

Reaction Occurred in the Reactor 106

The calcium carbide 208 produced from the chamber 105 then enters reactor 106. Water 209 supplied from water reservoir 113 is also supplied to the reactor 106. The calcium carbide 208 and the water 209 react to form acetylene gas 210 which is received in reactor 107. Please see below reaction (9).

$$CaC_2 + 2H_2O \rightarrow C_2H_2 + Ca(OH)_2 \quad (9)$$

Another product from the chamber 106 is calcium hydroxide 211. This calcium hydroxide 211 is then passed through a catalyst support regenerator 108 for generation of calcium oxide 221. Please see below reaction (10).

(10)

This calcium oxide 221 is channeled to the catalyst support supply/reservoir 102, for continuous use and circulation in the system, thus achieving a close loop production of ethylene 213 in the system.

Reaction Occurred in the Reactor 107

The acetylene gas 210 from reactor 106 can be reacted with the hydrogen gas 212 from the hydrogen supply/reservoir 109 in the reactor 107. Ethylene gas 213 is formed as a final product of the system. Please see below reaction (11).

$$C_2H_2 + H_2 \rightarrow C_2H_4 \quad (11)$$

In this embodiment, 162 kg ethylene is produced from the original feedstock waste 800. Table 4 below summarizes primary of ethylene production from the system.

TABLE 4

Primary ethylene production and other gaseous products

| 800 INPUT/hr | Mass (kg) | Chemical Energy (MW$_{chem}$) | CH$_4$ OUTPUT (m$^3$) | H$_2$ OUTPUT (m$^3$) | CO OUTPUT (m$^3$) | CO2 OUTPUT (m$^3$) |
|---|---|---|---|---|---|---|
| sewage sludge | 6,250 | 2.6 | 182 | | | 168 |
| F & K waste | 625 | 1.6 | 112 | | | 103 |
| RDF waste | 1,275 | 6.1 | 123 | 613 | 305 | 347 |
| Outputs | | | | | | |
| nano carbon | 208 | | −417 | 764 | | |
| CaO | 324 | | | | | |
| CaC2 | 370 | | | −375 | 141 | |
| C$_2$H$_4$ | 162 | | | −129 | | |
| sub total | | | 417 | 873 | 446 | 618 |

Decomposition of CO$_2$ Over Nano Carbon Produced

As shown in FIG. 2, nano carbon produced in reactor 104 and part of this nano carbon 206B can be reacted with part of the CO$_2$ generated 215C within the system in reactor 116. This process is called Boudouard reaction and reaction shows as below:

$$CO_2 + \text{nano carbon} \rightarrow 2CO$$

By decomposition of CO$_2$, the CO$_2$ generated in the close-loop process can be re-used. Referring to Table 4, CO$_2$ generated from waste has 618 m$^3$, and under Boudouard reaction it could generate approximately 16,000 m$^3$ CO. Such decomposition could be accomplished by external carbon feedstock 206C or the nano carbon generated from reactor 104.

Catalyst System Preparation in Laboratory Scale

The catalyst system comprises of catalyst and catalyst support. A step of deposition of the catalyst on the catalyst support can be performed by wet chemical impregnation using a solution with a VIII transition metal oxide or by deposition of volatile transition metal precursor complex with a metal oxidation state of zero.

Wet Impregnation

Catalyst is preferably selected from a group consisting of group VIII transition elements. The preferred elements are iron, nickel, cobalt, molybdenum or a mixture thereof, and in particular MoCo.

The catalyst support, acting like a carrier for catalyst, is advantageous in nano-catalyst preparation. Candidates for the catalyst support may be selected from a group including alkaline metal oxides, alkaline earth metal oxides, silicon, silicon oxides, aluminium oxide, silicon carbide, carbon materials like carbon nanotube and graphite and/or the mixtures thereof. Examples are silicates, olivines and ilmenite. The catalyst is preferably configured to possess a physical shape with high or higher surface area ratio, for example to assume a tubular or patelet morphology.

As an example, nickel may be used as a catalyst and silicon oxide (SiO$_2$) may be used as a catalyst support. In such example, nickel hydroxide (Ni(OH)$_2$) is prepared by mixing ammonia solution with aqueous nickel nitrate at pH 9. This pH can be archived by adding an appropriate amount of ammonia solution. In this reaction, nickel hydroxide is formed as a precipitate and can be observed. This precipitate is then isolated by using a filter funnel and the filtrate is then washed and deionized water and acetone. The filtrate is then dried in an oven overnight.

4.5 gram filtrate, Ni(OH)$_2$ is then dispersed in 100 ml acetone. Mixture is then vigorously stirred with 2 ml Tetraethoxysilan (TEOS), 5 ml de-ionised water and 2 ml ammonium hydroxide (25%). In such preparation, Ni(OH)$_2$ will be formed on top of SiO$_2$ as precipitate. Finally precipitate filtered and dried in oven.

Figure 4:
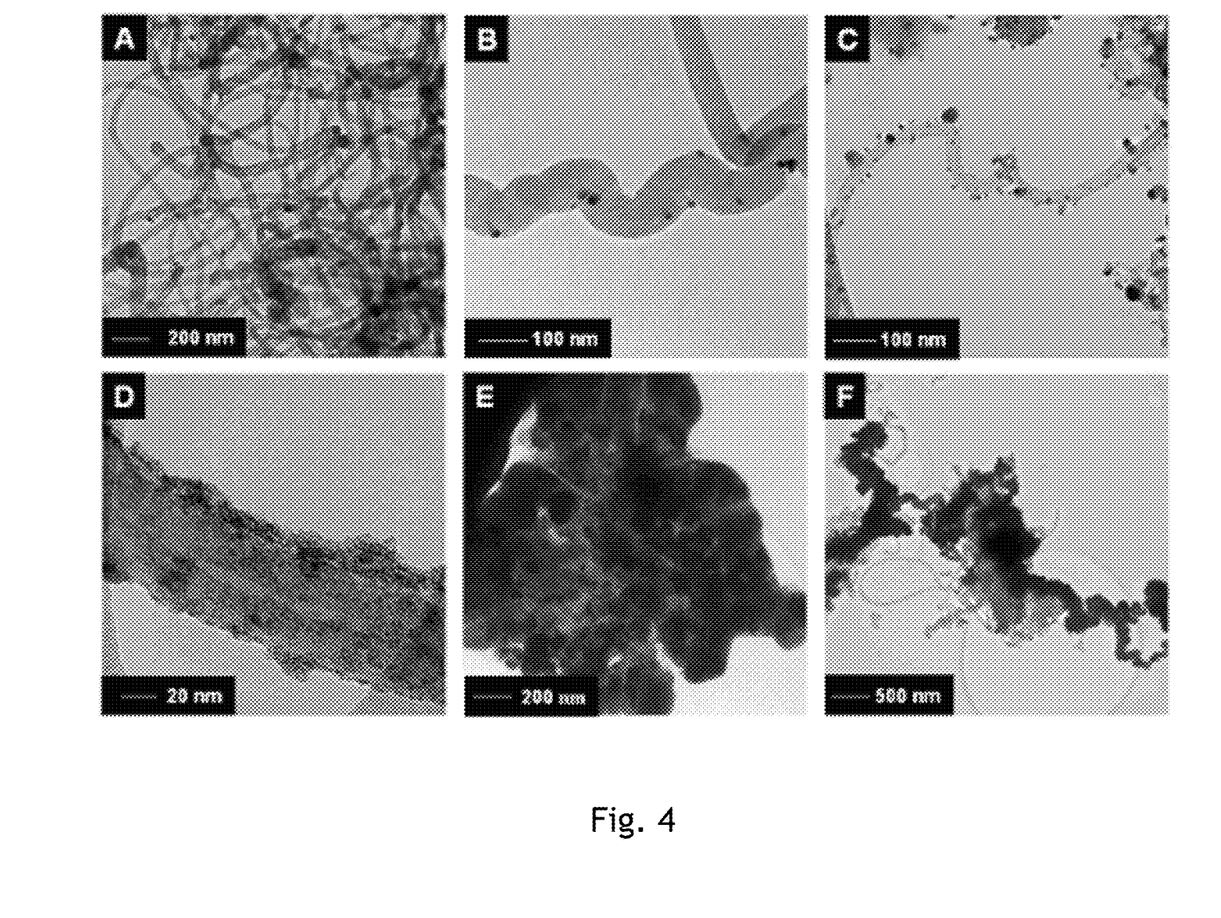
FIG. 4, including A, B, C, D, E and F, are SEM photographic images showing catalyst deposited on nano carbon (or carbon nanotubes by) using metal complex precursor method.

Metal Complex Precursor 0.5 g of pristine carbon nanotube is placed into a 2-necked 500 ml round bottom flask. The flask is vacuum for 15 mins using an electric pump, and then the flask is purged with N$_2$ for another 15 mins. The purging is repeated 2 times and the round bottom flask is then under a vacuum condition. Another 2-necked 50 ml round bottom flask is prepared and with the above described purging until vacuum is maintained. 0.1 ml Fe(CO)$_5$ is injected into the 50 ml round bottom flask and temperature is raised progressively to 75° C. A 2-side needle tubing is prepared and one needle is injected to the 50 ml round bottom flask while another side of needle is injected to the 500 ml round bottom flask. The 2-side needle tubing is disconnected after the system is left idling for 15 mins. The 500 ml round bottom flask is heated to 150° C. for 30 mins. SEM pictures of sample is shown in FIG. 4.

Production of Ethylene in Second Pathway in the System

From Table 4, it can be seen that 446 m$^3$ CO is produced from the system of FIG. 2. Please see the reservoir 114 supplied with carbon monoxide gases 207A, 224. The carbon monoxide 207B from reservoir 114 is output and subjected to water-gas shift (WGS) reaction in the reactor 111, and 408 m$^3$ hydrogen 216 is produced from the above amount CO. Please see below reaction (12).

$$CO + H_2O \rightarrow CO_2 + H_2 \tag{12}$$

Hydrogen produced from the system, together with the CO2 215B, originated from reservoir 115, are fed to the reactor 112 for Sabatier reaction (13). This reaction generates an additional 345 m$^3$ of methane.

$$CO_2 + 4H_2 \rightarrow 2H_2O + CH_4$$

This additional methane production is fed to the reactor 104, contributing to the supply of the methane gas required in the system. Table 5 below summarizes quantities of production of various gases in the system. Under this second pathway of utilizing the CO generated in the first pathway, additional 108 kg of ethylene can be produced.

TABLE 5

Production of ethylene and other gaseous products in second pathway production

| | mass (kg) | CH$_4$ OUTPUT (m$^3$) | H$_2$ OUTPUT (m$^3$) | CO OUTPUT (m$^3$) | CO2 OUTPUT (m$^3$) |
|---|---|---|---|---|---|
| WGS | | | 408 | −446 | 438 |
| Sabatier | | 345 | −1,280 | | −344 |
| nano carbon | 139 | −345 | 513 | | |
| CaO | 215 | | | | |
| CaC2 | 249 | | −248 | 94 | |
| C2H4 | 108 | | −86 | | |

Production of Ethylene in Third Pathway in the System

From Table 5, it is shown that 94 m$^3$ CO is produced though the second pathway of ethylene production from the system of FIG. 2. Carbon monoxide 207B from reservoir 114 are channeled to undergo water-gas shift reaction in the reactor 111, generating 86 m³ of hydrogen from the above said amount of CO.

$$CO + H_2O \rightarrow CO_2 + H_2 \quad (14)$$

Part of the hydrogen from reservoir 109 is fed into reactor 112 for Sabatier reaction in which additional methane 218 is collected and directed to the methane supply reservoir 110. 71 m³ of methane is produced in this reaction in this embodiment.

$$CO_2 + 4H_2 \rightarrow 2H_2O + CH_4 \quad (15)$$

This additional methane 218 contributes to the methane supply reservoir 110 for catalytic generation of nano carbon as explained above. Table 6 below summarizes production of ethylene due to use of the methane 218 from the third pathway. Under this third pathway of utilizing CO generated in the second pathway, additional 22 kg of ethylene could be produced.

TABLE 6

Production of ethylene and other gaseous products in third pathway production

| | mass (kg) | CH₄ OUTPUT (m³) | H₂ OUTPUT (m³) | CO OUTPUT (m³) | CO2 OUTPUT (m³) |
|---|---|---|---|---|---|
| WGS | | | 86 | −94 | 92 |
| Sabatier | | 71 | −263.4 | | −71 |
| nanocarbon | 29 | −71 | 106 | | |
| CaO | 44 | | | | |
| CaC2 | 51 | | −51 | 19.3 | |
| C2H4 | 22 | | −18 | | |

Production of Ethylene in First, Second and Third Pathways

The above tables show that in the experiment the total amount of ethylene production from original feedstock 800 is approximately 292 kg. Since the ethylene production is from hydrogenation of acetylene, therefore the above example should not be considered as a limitation to acetylene production.

It is to be noted that the input reactants required in the system are essentially the combustible and/or fermentable, the catalyst, the catalyst support and water. Once in operation, the system is other self-sustaining as far as input ingredients are concerned. Many of the other reactants required in the system are actually derived from within the system as intermediates. In other words, the system can be regarded as a close-loop system in producing ethylene gas from energy-rich product gases derived from decomposition of abundant organic matter like anaerobic digestion and gasification. Since waste treatment facilities usually are built in decentralized architecture and so our system could be used to produce ethylene in decentralized way. Economically, it reduces extra infrastructure cost in building up large centralized plants, requiring components out of standard productions' dimensions and for ethylene production and also logistically it is more economic, as logistic cost of ethylene or acetylene could be saved in de-centralized plants reducing risks for leakages in underground pipes that could be saved by going local.

Another advantage of this method and means is the potential of reusing atmospheric carbon feedstock from waste generated within a community or industry. The state of art energy recovery releases $CO_2$ and CO to the atmosphere often exceeding substituted energy generations' Carbon intensity or for no synchronous energy demand without a purpose use.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose.

SUMMARY OF TERMINOLOGY 101 transition metal catalyst reservoir
102 catalyst support reservoir
103 reactor I
104 reactor II
105 reactor III
106 reactor IV
107 reactor V
108 reactor VI
109 H₂ reservoir
110 CH₄ reservoir
111 reactor VII
112 reactor VIII
113 Water reservoir
114 CO reservoir
115 CO₂ reservoir
116 reactor IX
201 transition metal catalyst feedstock
201A transition metal catalyst before reactor I
202 catalyst support feedstock
202A catalyst support before reactor I
202B catalyst support before reactor III
203 catalyst system before reactor I
204 methane gas feed-in before reactor II
205 Hydrogen out of reactor II
206A Nano carbon before reactor III
206B Nano carbon before reactor IX
206C External carbon feedstock
207A Carbon Monoxide out of reactor III
207B CO after CO reservoir
208 CaC₂ out of reactor
209 Water before reactor IV
210 C₂H₂ out of reactor IV
211 Ca(OH)₂ out of reactor IV
212 H₂ before reactor V
213 C₂H₄ out of reactor V
214 water before reactor VII
215A CO₂ out of reactor VII
215B CO₂ before reactor VIII
215C CO₂ after reservoir 115
216 H₂ out of reactor VII
217 H₂ before reactor VIII
218 CH₄ out of reactor VIII
219 H₂O out of reactor VIII
220 H₂O feedstock
221 CaO after catalyst support regenerator
222A CH₄ feedstock after gasifier
222B CH₄ feedstock after anaerobic digester
223 H₂ after gasifier
224 CO after gasifier
225A CO₂ feedstock after gasifier
225B CO₂ feedstock after anaerobic digester
226 CO after reactor IX
800 Waste 801 Combustibles
802 Fermentables
901 Gasifier
902 Anaerobic digester

The invention claimed is:

1. A method of converting at least one of fermentable and combustible organic wastes to produce acetylene or ethylene in a system including a closed loop, comprising:
   a) providing supplies of hydrogen, water, carbon monoxide, and carbon dioxide;
   b) providing a supply of methane;
   c) providing a catalyst system having firstly a catalyst selected from group VIII transition metal oxides, and secondly a catalyst support;
   d) treating said methane supply with said catalyst system for producing carbon;
   e) providing calcium oxide;
   f) reacting said carbon with said calcium oxide for producing an intermediate; and
   g) reacting said intermediate with water to produce acetylene, and optionally subjecting the produced acetylene to hydrogenation to produce ethylene;
   wherein:
   the supplies of hydrogen, water, carbon monoxide, carbon dioxide and methane are contributed from sources including the organic wastes;
   said intermediate is calcium carbide ($CaC_2$);
   each of said methane supply and said carbon dioxide supply is derived from a combination of an external source and an internal source thereof yielded during said acetylene or ethylene production, said combination of said external and internal sources reacting during said acetylene or ethylene production to contribute to said supplies of hydrogen, water, carbon monoxide, carbon dioxide, and methane, for subsequent consumption in said acetylene or ethylene production; and
   said carbon dioxide passes through said closed loop.

2. A method as claimed in claim 1, wherein said catalyst is an oxide of nickel, cobalt, or iron, or a combination thereof.

3. A method as claimed in claim 1, wherein said catalyst is selected from a group including iron, nickel, cobalt and molybdenum.

4. A method as claimed in claim 1, wherein said catalyst support is selected from a group including alkaline metal oxides, alkaline earth metal oxides, silicon, silicon oxides, aluminium oxides, silicon carbide, carbon and a mixture thereof, wherein said catalyst support has tubular or platelet morphology for increasing surface area thereof.

5. A method as claimed in claim 1, comprising depositing said catalyst on said catalyst support by wet chemical impregnation of a solution with a group VIII transition metal oxide.

6. A method as claimed in claim 1, wherein said catalyst is deposited on catalyst support by decomposition of a volatile transition metal precursor complex comprising depositing said catalyst on said catalyst support by decomposition of a volatile transition metal precursor, wherein metal in said metal precursor complex has an oxidation state of zero.

7. A method as claimed in claim 1, comprising acquiring a first energy containing feedstock substrate, wherein said first energy containing feedstock substrate includes fermentables, wherein said fermentables include sewage sludge, food and kitchen waste or a combination thereof, the method further comprising subjecting the first energy containing feedstock substrate to anaerobic digestion for production of said carbon dioxide and said methane and for contribution to said external source of said carbon dioxide and said methane supplies, respectively.

8. A method as claimed in claim 1, comprising acquiring a second energy containing feedstock substrate, wherein said second energy containing feedstock substrate includes combustibles,
   wherein said combustibles include refuse derived fuel, coal, biomass, fermentation digestible or a combination thereof, and/or
   wherein said second energy containing feedstock has an input caloric value of at least 10 GJ/t.

9. A method as claimed in claim 8, comprising subjecting said second energy containing feedstock substrate to thermo-chemical treatment for production of said methane, said hydrogen, said carbon monoxide, and said carbon dioxide and for contribution to said external source of said methane, said hydrogen, said carbon monoxide, and said carbon dioxide, respectively.

10. A method as claimed in claim 1, comprising, during formation of nano carbon in said step d) in claim 1, cracking said methane supply for yielding a first said internal source of said hydrogen, said first internal hydrogen source contributing to said hydrogen supply in said step a) in claim 1, further comprising, during formation of said calcium carbide ($CaC_2$), reacting said nano carbon with said calcium oxide for yielding said internal source of said carbon monoxide, said internal source of carbon monoxide contributing to said carbon monoxide supply.

11. A method as claimed in claim 1, comprising:
   subjecting said carbon monoxide supply to water-gas shift reaction for yielding a second said internal source of said hydrogen and a first said internal source of said carbon dioxide, and said second internal source of hydrogen and said first internal source of carbon dioxide contributing to said hydrogen supply and said carbon dioxide supplies, respectively;
   subjecting said hydrogen supply and said carbon dioxide supply to Sabatier reaction, for yielding a first said internal source of methane and said internal source of water, said first internal source of methane contributing to said methane supply and said internal source of water for contributing to said methane supply and said water supply, respectively;
   subjecting nano carbon and said carbon dioxide supply to Boudouard reaction, for yielding carbon monoxide contributing to said carbon monoxide supply;
   splitting hydrocarbon gas and providing heating required in said splitting of hydrocarbon gas, wherein said heating is derived from waste heat internally or externally; and
   reusing external hydrocarbon gas at least partially from the organic wastes for production of methane contributing to said methane supply.

12. A method as claimed in claim 4, wherein said catalyst support is calcium oxide.

13. A method as claimed in claim 1, comprising subjecting said hydrogen supply and said carbon dioxide supply to a Sabatier reaction yielding methane contributing to said methane supply and water contributing to said water supply.

14. A method as claimed in claim 1, comprising subjecting said carbon monoxide supply to a water-gas shift reaction yielding hydrogen contributing to said hydrogen supply and carbon dioxide contributing to said carbon dioxide supply.

* * * * *